US008221486B2

(12) United States Patent
Thistle

(10) Patent No.: US 8,221,486 B2
(45) Date of Patent: Jul. 17, 2012

(54) LAMINATED STENT GRAFT EDGE BINDING

(75) Inventor: Robert C. Thistle, Bridgewater, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 865 days.

(21) Appl. No.: 11/602,742

(22) Filed: Nov. 21, 2006

(65) Prior Publication Data

US 2008/0119924 A1    May 22, 2008

(51) Int. Cl.
    *A61F 2/06* (2006.01)
(52) U.S. Cl. ............... 623/1.13; 623/1.15; 623/1.16
(58) Field of Classification Search ............. 623/1.12, 623/1.16, 1.18, 1.42
    See application file for complete search history.

(56) References Cited

U.S. PATENT DOCUMENTS

2003/0116260 A1*  6/2003  Chobotov et al. .......... 156/217

FOREIGN PATENT DOCUMENTS

WO      9826731       6/1998

OTHER PUBLICATIONS

PCT International Search Report for International Application No. PCT/US2007/085419, dated Jun. 5, 2008, 3 pages.

* cited by examiner

*Primary Examiner* — Thomas J Sweet
*Assistant Examiner* — Joshua Levine
(74) *Attorney, Agent, or Firm* — Vidas, Arrett & Steinkraus, P.A.

(57) ABSTRACT

A method of making a stent-graft comprising, providing a radially distensible, tubular stent having opposed open ends comprising an undulating wire helically wound into a plurality of circumferential windings to define stent wall structure having opposed exterior and luminal surfaces, providing a first non-textile, polymeric graft tube, providing a second non-textile, polymeric graft tube, laminating the radially distensible, tubular stent between the first non-textile, polymeric graft tube and the second non-textile, polymeric graft tube, trimming the laminated polymeric graft tube beyond the undulating wire at the open ends, providing a third non-textile, polymeric graft layer; placing the third non-textile, polymeric graft layer over the trimmed over ends, inserting the third non-textile, polymeric graft layer of the tubular stent into the undulating wires; and laminating the third non-textile polymeric graft layer to the first non-textile, polymeric graft tube and the second non-textile, polymeric graft tube.

4 Claims, 2 Drawing Sheets

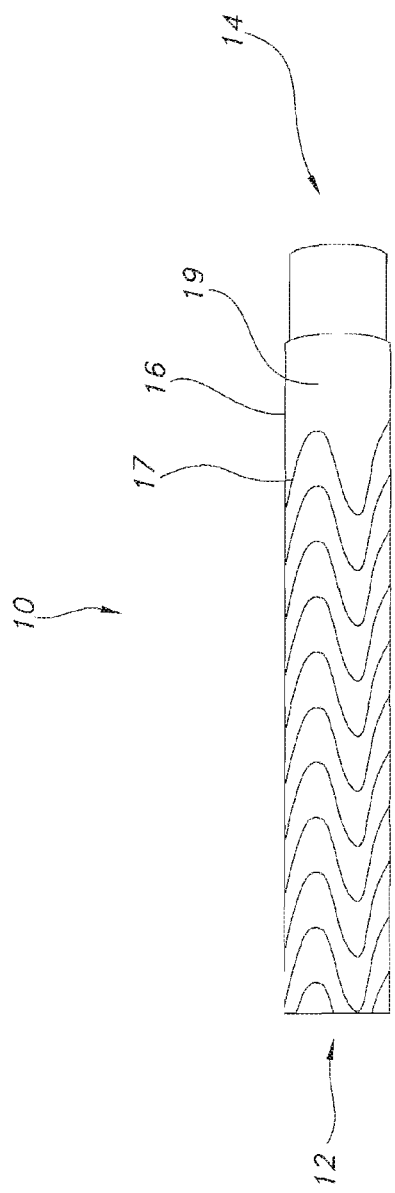
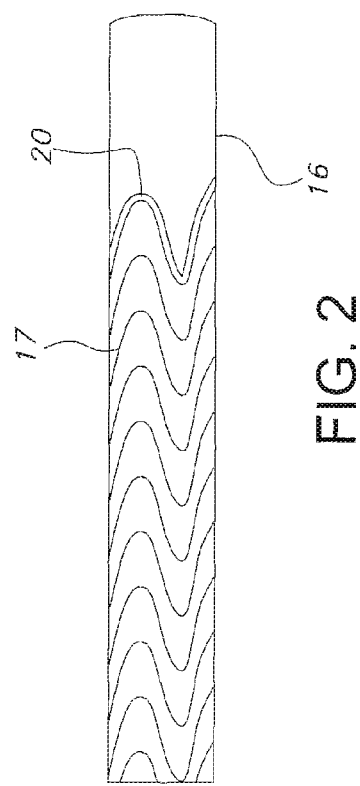

LAMINATED STENT GRAFT EDGE BINDING

FIELD OF THE INVENTION

The present invention relates to a method of making a laminated stent graft device that will reduce delaminating of the open ends by the application of an edge binding.

BACKGROUND OF THE INVENTION

An intraluminal prosthesis is a medical device used in the treatment of diseased bodily lumens. One type of intraluminal prosthesis used in the repair and/or treatment of diseases in various body vessels is a stent. A stent is generally a longitudinal tubular device formed of biocompatible material which is useful to open and support various lumens in the body. For example, stents may be used in the vascular system, urogenital tract, esophageal tract, tracheal/bronchial tubes and bile duct, as well as in a variety of other applications in the body. These devices are implanted within the vessel to open and/or reinforce collapsing or partially occluded sections of the lumen.

Stents generally include an open flexible configuration. This configuration allows the stent to be inserted through curved vessels. Furthermore, this configuration allows the stent to be configured in a radially compressed state for intraluminal catheter implantation. Once properly positioned adjacent the damaged vessel, the stent is radially expanded so as to support and reinforce the vessel. Radial expansion of the stent may be accomplished by inflation of a balloon attached to the catheter or the stent may be of the self-expanding variety which will radially expand once deployed. Tubular shaped structures, which have been used as intraluminal vascular stents, have included helically wound coils which may have undulations or zig-zags therein, slotted stents, ring stents, braided stents and open mesh wire stents, to name a few. Super-elastic materials and metallic shape memory materials have also been used to form stents.

A graft is another commonly known type of intraluminal prosthesis which is used to repair and replace various body vessels. A graft provides a lumen through which fluids, such as blood, may flow. Moreover, a graft is often configured as being generally impermeable to blood to inhibit substantial leakage of blood therethrough. Grafts are typically hollow tubular devices that may be formed of a variety of materials, including textile and non-textile materials.

A stent and a graft may be combined into a stent-graft endoprosthesis to combine the features and advantages of each. For example, tubular coverings have been provided on the inner and/or outer surfaces of stents to form stent-grafts. It is often desirable to use a thin-walled graft or covering in the stent-graft endoprosthesis to minimize the profile of the endoprosthesis and to maximize the flow of blood through the endoprosthesis. In such cases non-textile materials, such as polymeric tubes or sheets formed into tubes, are often used. Expanded polytetrafluoroethylene or e-PTFE is one common polymeric material used as the graft portion or covering of a stent-graft endoprosthesis. Expanded polytetrafluoroethylene grafts, however, are subject to plastic deformation, especially when, for example, compressing the stent-graft for loading into its delivery system, delivering the stent-graft through a highly tortuous bodily lumen and/or placing or deploying the stent-graft at the target implant site. Such plastic deformation may lead to the tearing of the ePTFE, leaving the stent-graft endoprosthesis prone to leakage of blood therethrough. Furthermore, plastic deformation of expanded polytetrafluoroethylene grafts may lead to physical deformities in the graft, such as buckling, which is also undesirable because it may lead to poor blood flow patterns.

Sheets or films of ePTFE have been used to cover or line stents. For example, U.S. Pat. Nos. 5,700,285 and 5,735,892 to Myers et al. describe overlapping a sheet of ePTFE onto a stent to form a tubular graft. The graft is secured to the stent by an application of thermoplastic adhesive and heat treatment to melt the adhesive. A seam, which is formed where the sheet overlaps, is also sealed through the use of the thermoplastic adhesive. Such stent-grafts having a unitary tubular ePTFE covering adhesively secured to the stent, however, do not have flexibility associated with the graft to avoid plastic deformation of the graft when subjected to certain stresses, such as bending stresses during delivery through tortuous bodily lumens.

U.S. Pat. No. 6,264,684 to Banas et al. describes a helically supported ePTFE graft, i.e., a stent-graft. The support or stent wire is encapsulated in an ePTFE strip. The strip is helically wound over a mandrel into a configuration having adjacent windings forming overlapping regions. The overlapping regions are secured to one and the other through the use of a thermoplastic adhesive and a heat treatment for melting the thermoplastic adhesive. U.S. Pat. No. 6,790,225 to Shannon et al. describes the helically winding of ePTFE tape to completely cover a stent and sintering the tape to the stent. Any overlaps of the ePTFE tape are also sintered together.

Typically part of the manufacturing is a process known as scalloping. This is the trimming of the laminated covering that is performed around the wires at the ends of the stent. The scalloping is performed by making a constant scallop length around the tracing of the diameter just beyond the stent wires. However, the scallop area can be prone to delaminating when subjected to contact, such as contact from the delivery system sheath during loading, should the scallop length be too short.

Thus, there is a need for a stent-graft having a polymeric, non-textile graft having a cut free binding of the scalloped laminated edge that will prevent delaminating of the edge.

SUMMARY OF THE INVENTION

In one aspect of the present invention, there is provided a method of making a stent-graft comprising, providing a radially distensible, tubular stent having opposed open ends comprising an undulating wire helically wound into a plurality of circumferential windings to define stent wall structure having opposed exterior and luminal surfaces, providing a first non-textile, polymeric graft tube, providing a second non-textile, polymeric graft tube, laminating the radially distensible, tubular stent between the the first non-textile, polymeric graft tube and the second non-textile, polymeric graft tube, trimming the laminated polymeric graft tube beyond the undulating wire at the open ends, providing a third non-textile, polymeric graft layer; placing the third non-textile, polymeric graft layer over the trimmed over ends, inserting the third non-textile, polymeric graft layer of the tubular stent into the undulating wires; and laminating the third non-textile polymeric graft layer to the first non-textile, polymeric graft tube and the second non-textile, polymeric graft tube.

In another aspect of the current invention there is provided a method of making a stent-graft comprising, providing a radially distensible, tubular stent having opposed open ends comprising an undulating wire helically wound into a plurality of circumferential windings to define stent wall structure having opposed exterior and luminal surfaces, providing a first non-textile, polymeric graft tube, providing a second non-textile, polymeric graft tube, laminating said radially distensible, tubular stent between said first non-textile, polymeric graft tube and said second non-textile, polymeric graft tube, trimming said second non-textile, polymeric graft tube along said undulating wire at said open ends, folding said first non-textile; polymeric graft tube over said radially distensible tubular stent, laminating said radially distensible, tubular stent between said first non-textile, polymeric graft tube and said second non-textile, polymeric graft tube.

In yet another aspect of the current invention there is provided a a radially distensible, tubular stent having opposed open ends comprising an undulating wire helically wound into a plurality of circumferential windings to define stent wall structure having opposed exterior and luminal surfaces, a first non-textile, polymeric graft tube laminated within the luminal surface, and a second non-textile, polymeric graft tube laminated to the exterior surface to define an outer wall, wherein the a first non-textile, polymeric graft tube and the second non-textile polymeric graft tube are folded back over the undulating wire at the open ends, and laminated to the outer wall at the open ends.

BRIEF DESCRIPTION OF THE DRAWINGS

FIG. 1 is a side view of a stent-graft according to the present invention post lamination.

FIG. 2 is a side view of a stent-graft according to the present invention post scalloping.

FIG. 3A is a side view of the stent graft components according to the current invention prior to assembly.

DETAILED DESCRIPTION OF THE PREFERRED EMBODIMENT

Figure 3B:
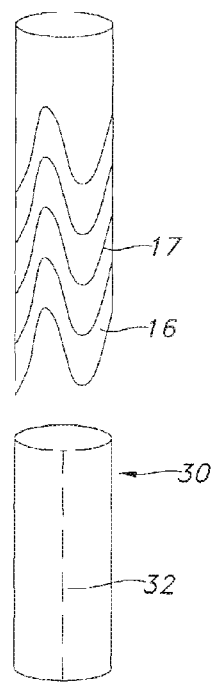
FIG. 3B is a side view of the stent graft components according to the current invention after assemble.

FIG. 1 is a side view of the stent-graft 10 of the present invention. The stent-graft 10 is a hollow, tubular structure or device having opposed open ends 12, 14. The stent-graft 10 includes a tubular wall 16 disposed between the open ends 12, 14. As depicted in FIG. 1, the tubular wall 16 extends along the longitudinal direction. The stent-graft device of the present invention includes a helically wound wire stent device having an equally spaced undulating or zig-zag pattern. The zig-zag pattern is an equally spaced pattern of helically wound wire nesting throughout the design by a spiral of the zigs along the longitudinal direction of the stent graft device. The zigs are formed of a wire which is helically wound around the as depicted in FIG. 1, stent-graft 10 is a substantially longitudinally straight tubular device, but the present invention is not so limited. Stent-graft 10 may have a varying radial extent, for example, a varied diameter, outwardly or inwardly flared extents, and the like. Furthermore, the zig-zag pattern dimensions are relative to the nominal dimensions of the stent-graft device.

As can be seen in FIG. 1, there is a length of laminated tubular wall 16 beyond the end of the stent structure 17, prior to the scalloping operation. The scalloping operation includes the trimming of the laminated cover 19 that extends beyond stent structure 17. In accordance with the present invention, the stent graft 10 is formed using a lamination procedure as further described hereinafter and known in the art. As shown in FIG. 2, once the lamination procedure is completed, the trimming is performed around the wires of stent structure 17 by rough trimming a scallop 20 around the stent structure 17. After scalloping, a length of tubular wall 16 extends beyond stent structure 17. Once the scalloping is complete an additional tubular structure, typically formed of ePTFE, having an inner diameter slightly larger than the outer diameter of the stent wires is slit along the length of the tubing, and then placed onto the trimmed edge of the stent graft 10 along the entire tracing of the scalloped edge. Once the tubing is placed over the stent structure 17, the stent wires are placed into the slit in the tubing and an additional lamination step is performed to bind the tubing to the inner and outer ePTFE covering.

As depicted in FIG. 1, the stent-graft 10 may include a stent 17. Various stent types and stent constructions may be employed in the invention as the stent 17. Among the various stents useful include, without limitation, self-expanding stents and balloon expandable extents. The stents may be capable of radially contracting, as well and in this sense can best be described as radially distensible or deformable. Self-expanding stents include those that have a spring-like action which causes the stent to radially expand, or stents which expand due to the memory properties of the stent material for a particular configuration at a certain temperature. Nitinol is one material which has the ability to perform well while both in spring-like mode, as well as in a memory mode based on temperature. Other materials are of course contemplated, such as stainless steel, platinum, gold, titanium and other biocompatible metals, as well as polymeric stents. The configuration of the stent may also be chosen from a host of geometries. For example, wire stents can be fastened into a continuous helical pattern, with or without a wave-like or zig-zag in the wire, to form a radially deformable stent. Individual rings or circular members can be linked together such as by struts, sutures, welding or interlacing or locking of the rings to form a tubular stent. Tubular stents useful in the present invention also include those formed by etching or cutting a pattern from a tube. Such stents are often referred to as slotted stents. Furthermore, stents may be formed by etching a pattern into a material or mold and depositing stent material in the pattern, such as by chemical vapor deposition or the like. Examples of various stent configurations are shown in U.S. Pat. Nos. 4,503,569 to Dotter; U.S. Pat. No. 4,733,665 to Palmaz; U.S. Pat. No. 4,856,561 to Hillstead; 4,580,568 to Gianturco; U.S. Pat. No. 4,732,152 to Wallsten, U.S. Pat. No. 4,886,062 to Wiktor, and U.S. Pat. No. 5,876,448 to Thompson, all of whose contents are incorporated herein by reference.

Desirably, stent 17 is one that has minimal foreshortening, i.e., a stent wherein its longitudinal length remains substantially constant upon radial expansion or radial contraction of the stent. As depicted in FIG. 1, such a stent 17 having minimal foreshortening may include a zig-zag pattern.

Desirably, the stent 17 is made from any suitable implantable, biocompatible, bioabsorbable or biodegradable material, including without limitation nitinol, stainless steel, cobalt-based alloy such as Elgiloy®, platinum, gold, titanium, tantalum, niobium, polymeric materials and combinations thereof. Useful and nonlimiting examples of polymeric stent materials include poly(L-lactide) (PLLA), poly(D,L-lactide) (PLA), poly(glycolide) (PGA), poly(L-lactide-co-D, L-lactide) (PLLA/PLA), poly(L-lactide-co-glycolide) (PLLA/PGA), poly(D,L-lactide-co-glycolide) (PLA/PGA), poly(glycolide-co-trimethylene carbonate) (PGA/PTMC), polydioxanone (PDS), Polycaprolactone (PCL), polyhydroxybutyrate (PHBT), poly(phosphazene) poly(D,L-lactide-co-caprolactone) PLA/PCL), poly(glycolide-co-caprolactone) (PGA/PCL), poly(phosphate ester) and the like.

Further, the stent 17 may have a composite construction, such as described found in U.S. Patent Application Publication 2002/0035396 A1, the contents of which is incorporated herein by reference. For example, the stent 17 may have an inner core of tantalum gold, platinum, iridium or combination of thereof and an outer member or layer of nitinol to provide a composite wire for improved radiocapacity or visibility. Alternatively, a radiopaque member or wire may be secured to a portion of the stent 17 for improved radiocapacity or visibility.

Figure 3C:
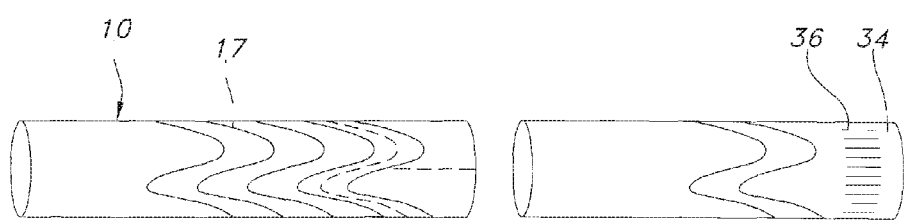
FIG. 3C is a side view of the stent graft components according to an alternated embodiment of the current invention.

Turning now to FIG. 3A, there is shown a diagram of the stent graft 10, after the lamination and scalloping step showing the stent structure 17 and tubular wall 16, extending beyond the stent structure 17. Also shown is a length of tubing 30 having a slit 32 along its length. As described above, the inner diameter of tubing 30 is slightly large than the outer diameter of the stent wires prior to slit 32 being made in tubing 30. Turning now to FIG. 3B there is shown the stent graft 10 having tube 30 placed over the scalloped end of tubular wall 16, with stent wires 17 placed into slit 32 of the tubing 30. Once positioned as in FIG. 3B, the assemble would receive an additional lamination cycle in order to bind the tubing to the inner and outer ePTFE tubing. Turning now to FIG. 3C there is shown an alternate embodiment of the present invention. In this alternate embodiment, the inner ePTFE tubing 34 is extended beyond the stent frame, and the outer ePTFE tubing is cut to follow the stent frame. Prior to lamination, the inner layer is then folded up over the end of the stent to cover the outer tubing and stent. Relief cuts 36 are made in the inner layer 34 to allow it to closely conform to the outer stent wires. While longitudinal relief cuts are shown it is contemplated that relief cuts of other orientations, are possible.

The non-textile, polymeric tubular body 16 may suitably be made from extruded, molded or cast polymeric materials. As used herein, the term "textile" refers to a material, such as a yarn, that has been knitted, woven, braided and the like into a structure, including a hollow, tubular structure. As used herein, the term "non-textile" and its variants refer to a material formed by casting, molding, spinning or extruding techniques to the exclusion of typical textile forming techniques, such as braiding, weaving, knitting and the like. Nonlimiting examples of useful polymeric materials for the non-textile polymeric graft portions include polyesters, polypropylenes, polyethylenes, polyurethanes, polynaphthalenes, polytetrafluoroethylenes, expanded polytetrafluoroethylene, silicone, and combinations and copolymers thereof. Desirably, the polymeric material polytetrafluoroethylene (PTFE), including expanded polytetrafluoroethylene (ePTFE).

PTFE exhibits superior biocompatibility and low thrombogenicity, which makes it particularly useful as vascular graft material in the repair or replacement of blood vessels or other bodily lumens. Desirably the non-textile layer is a tubular structure manufactured from ePTFE. The ePTFE material has a fibrous state which is defined by interspaced nodes interconnected by elongated fibrils. The space between the node surfaces that is spanned by the fibrils is defined as the internodal distance. When the term expanded is used to describe PTFE, it is intended to describe PTFE which has been stretched, in accordance with techniques which increase the internodal distance and concomitantly porosity. The stretching may be in uni-axially, bi-axially, or multi-axially. The nodes are spaced apart by the stretched fibrils in the direction of the expansion.

Desirably, the ePTFE material is a physically modified ePTFE tubular structure having enhanced axial elongation and radial expansion properties of up to about 2,000 percent by linear dimension, for example, from about 100 percent by linear dimension to about 2,000 percent by linear dimension, from about 100 percent by linear dimension to about 600 percent by linear dimension, from about 600 percent by linear dimension to about 2,000 percent by linear dimension, and the like. Such expansion properties are not limiting. Such physically modified ePTFE material may be made by reorienting the node and fibril structure through application a radially expansive and longitudinally foreshortening force. The physically modified ePTFE tubular structure is able to be elongated or expanded and then returned to its original state without an elastic force existing therewithin. Additional details of the physically modified ePTFE and methods for making the same can be found in U.S. Pat. No. 6,716,239, the contents of which are incorporated by reference herein.

The non-textile, polymeric graft tubular body 16 of the present invention may be secured to one and the other and/or secured to the stent structure 17 through any suitable means, including, without limitation, lamination, such as heat and/or pressure lamination, and/or adhesive bonding. The bonding agent may include various biocompatible, elastomeric bonding agents such as urethanes, styrene/isobutylene/styrene block copolymers (SIBS), silicones, and combinations thereof. Other similar materials are contemplated. Desirably, the bonding agent may include polycarbonate urethanes sold under the trade name CORETHANE®. This urethane is provided as an adhesive solution with preferably 7.5% Corethane, 2.5 W30, in dimethylacetamide (DMAc) solvent. Details of suitable bonding agents and methods for bonding are further described in U.S. Patent Application Publication Nos. 2003/0017775 A1 and 2004/0182511 A1, the contents of which are incorporated herein by reference.

With any embodiment, the stent-graft 10 may be used for a number of purposes including to maintain patency of a body lumen, vessel or conduit, such as in the coronary or peripheral vasculature, esophagus, trachea, bronchi colon, biliary tract, urinary tract, prostate, brain, and the like. The devices of the present invention may also be used to support a weakened body lumen, or to provide a fluid-tight conduit for a body lumen, or support a weakened or kinked device in a lumen, for example adjunctive use. Adjunctive use involved the deployment of a second device, for example stent-graft 10, to a target site having a device, such as a stent, a graft or stent-graft previously positioned thereat. The stent-graft 10 of the present invention may be used to completely or partially overlap the previous device to alleviate a weakening or a kinking of the previous device, i.e., adjunctive deployment or adjunctive use.

Also, the stent-graft 10 may be treated with any known or useful bioactive agent or drug including without limitation the following: anti-thrombogenic agents (such as heparin, heparin derivatives, urokinase, and PPack (dextrophenylalanine proline arginine chloromethylketone); anti-proliferative agents (such as enoxaprin, angiopeptin, or monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); anti-neoplastic/antiproliferative/anti-miotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides); vascular cell growth promotors (such as growth factor inhibitors, growth factor receptor antagonists, transcriptional activators, and translational promotors); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vascoactive mechanisms.

The invention being thus described, it will now be evident to those skilled in the art that the same may be varied in many ways. Such variations are not to be regarded as a departure from the spirit and scope of the invention and all such modifications are intended to be included within the scope of the following claims.

What is claimed is:

1. A method of making a stent-graft comprising:
   providing a radially distensible, tubular stent having opposed first and second open ends, the stent comprising an undulating wire helically wound into a plurality of circumferential windings to define a stent wall structure having opposed exterior and luminal surfaces;
   providing a first non-textile, polymeric graft tube;
   providing a second non-textile, polymeric graft tube;
   laminating said radially distensible, tubular stent between said first non-textile, polymeric graft tube and said second non-textile, polymeric graft tube;
   trimming said laminated polymeric graft tube beyond said undulating wire at said first and second open ends of said tubular stent;
   providing a third non-textile, polymeric graft layer;
   cutting said third non-textile, polymeric graft layer to form a single longitudinal slit extending the entire length of said third non-textile polymeric graft layer;
   placing said third non-textile, polymeric graft layer over said trimmed ends;
   folding said third non-textile, polymeric graft layer over said undulating wire at said first and second open ends of said tubular stent; and
   laminating said third non-textile polymeric graft layer to said first non-textile, polymeric graft tube and said second non-textile, polymeric graft tube.

2. The method of making a stent graft of claim 1, wherein trimming said laminated polymeric graft tube beyond said undulating wire at said open ends includes trimming along said undulating wire.

3. The method of making a stent graft of claim 1, wherein said third non-textile, polymeric graft layer is a tube.

4. The method of making a stent graft of claim 1, wherein said third non-textile polymeric graft tube has an inner diameter slightly larger than the outer diameter of said stent wall.

\* \* \* \* \*